United States Patent [19]

Seal et al.

[11] Patent Number: 4,699,142
[45] Date of Patent: Oct. 13, 1987

[54] MICROSURGICAL SUTURE NEEDLES

[75] Inventors: Michael Seal, Amsterdam; Franciscus M. Berkhout, Cuyk, both of Netherlands

[73] Assignee: D. Drukker & Zn. N.V., Amsterdam, Netherlands

[21] Appl. No.: 876,181

[22] Filed: Jun. 19, 1986

[30] Foreign Application Priority Data

Jun. 21, 1985 [NL] Netherlands .................. 8501786

[51] Int. Cl.⁴ ............................................. A61B 17/06
[52] U.S. Cl. .............................. 128/339; 76/DIG. 12
[58] Field of Search ......................... 228/124 R, 122; 76/DIG. 12; 128/339

[56] References Cited

U.S. PATENT DOCUMENTS

| | | | |
|---|---|---|---|
| 1,321,011 | 11/1919 | Cottes | 128/339 |
| 3,192,620 | 7/1965 | Huizing et al. | 228/122 |
| 3,465,416 | 9/1969 | Wellborn | 228/124 R |
| 3,856,480 | 12/1974 | Johnson et al. | 228/122 |
| 3,868,750 | 3/1975 | Ellis et al. | 76/DIG. 12 |
| 3,937,222 | 2/1976 | Banko | 128/305 |
| 3,940,050 | 2/1976 | Johnson | 228/122 |

FOREIGN PATENT DOCUMENTS

| | | |
|---|---|---|
| 3118673 | 4/1982 | Fed. Rep. of Germany . |
| 185052 | 9/1922 | United Kingdom . |
| 2091624 | 1/1982 | United Kingdom . |

Primary Examiner—Richard C. Pinkham
Assistant Examiner—Gary Jackson
Attorney, Agent, or Firm—Pahl, Lorusso & Loud

[57] ABSTRACT

Microsurgical suture needles are made by providing a precious stone plate with main surfaces extending obliquely with respect to the longitudinal axis. A metal shank is provided with an end face extending correspondingly obliquely with respect to its longitudinal axis. The precious stone plate is attached with one main surface on the oblique end face of the metal shank. The other main surface of the precious stone plate is ground and provided with a sharp tip and cutting edges.

3 Claims, 4 Drawing Figures

MICROSURGICAL SUTURE NEEDLES

The invention relates to microsurgical suture needles.

The usual microsurgical suture needles are made completely from metal. In particular in eye surgery the suture of wounds by means of such a suture needle is an operation which should be done with the utmost care as uncontrolled movements may have serious consequences.

The invention aims to provide microsurgical suture needles by which suture needles are obtained which are easier to handle by the surgeon.

According to the invention a precious stone plate is formed with main surfaces extending obliquely with respect to the longitudinal axis, an end face extending correspondingly obliquely with respect to the longitudinal axis being ground at one end of a metal shank, on which the precious stone plate is attached with one main surface on the oblique end face of the metal shank, whereafter the other main surface of the precious stone plate is ground and provided with a sharp tip and cutting edges.

Thereby a suture needle can be obtained having a tip substantially sharper as compared to the known completely metal needles, and having cutting edges whereby the penetration capacity of the suture needle in the tissue is significantly increased. The pressure which has to be exerted on the suture needle in order to penetrate the tissue is thereby substantially less so that uncontrolled movements are reduced and the edges of the eye wound will deform less during the suture. Thereby the chance of losing intraocular fluid is reduced. Moreover the suture needle according to the invention produces smaller wounds so that the recovery is affected favourably and the deformation of the eyeball will be less.

Preferably a recess is cut out of the main surface of the precious stone plate to be attached to the metal shank. With a suture needle made in this manner a special suture method can be used whereby it is possible to hold the suture needle in a pair of tweezers and pick up the thread without the necessity of passing the needle completely through the wound as is necessary in the usual suture methods. Moreover in this case it is also possible to use the suture needle several times. The suture needle can be reground after some time.

The microsurgical suture needle according to the invention is characterized by a metal shank with a curved end part and a precious stone plate attached to the end face thereof extending obliquely with respect to its longitudinal axis, said precious stone plate having main surfaces extending correspondingly obliquely with respect to its longitudinal axis and said precious stone plate being provided with a ground tip and cutting edges.

The invention will hereinafter be further explained by reference to the drawings in which some embodiments of the suture needle according to the invention are shown.

Figure 1:
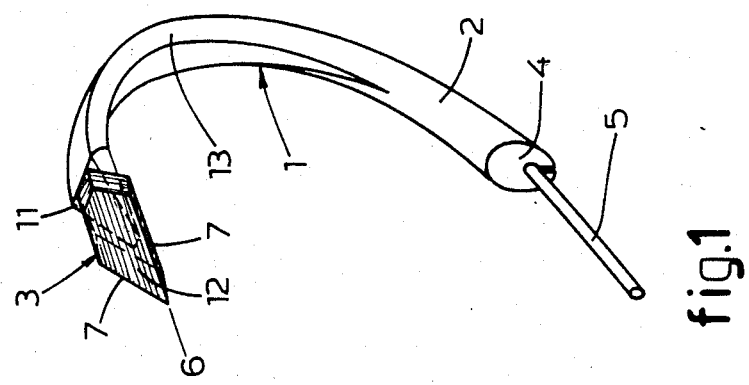
FIG. 1 is a perspective view of an embodiment according to the invention of the suture needle connected with a suture thread.

Referring to FIG. 1 there is shown a perspective view of a suture needle 1 consisting of a metal shank 2 and a diamond plate 3 attached to one end thereof. The other end 4 of the shank 2 is permanently connected with a suture thread 5.

In the embodiment shown in the drawings the cross-section of the metal shank 2 varies from substantially circular at the end 4 to substantially rectangular towards the diamond plate 3. The cross-section of the shank may however also be continuously circular or rectangular whereas other cross-section shapes are also possible.

The diamond 3 has a sharp tip 6 and cutting edges 7. As the suture thread 5 is permanently connected with the suture needle 1, the suture needle shown in FIG. 1 is only suited for use once.

Figure 2:
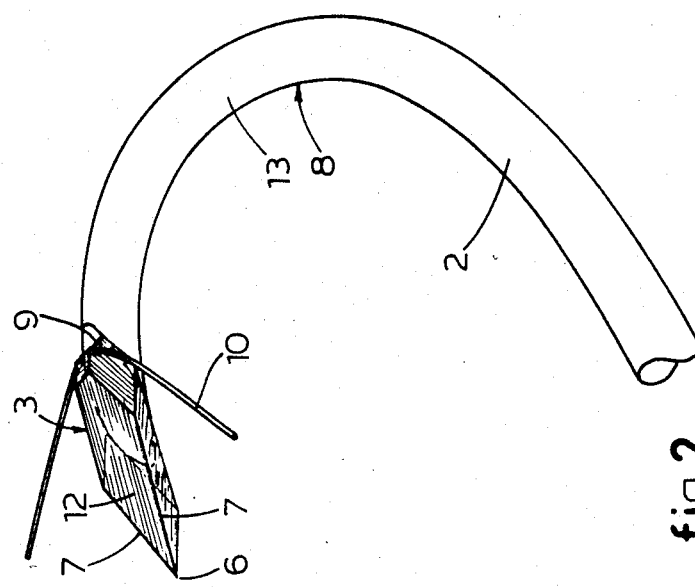
FIG. 2 is a perspective view of the end portion of a suture needle according to the invention which is very suitable for repeated use.
Figure 3:
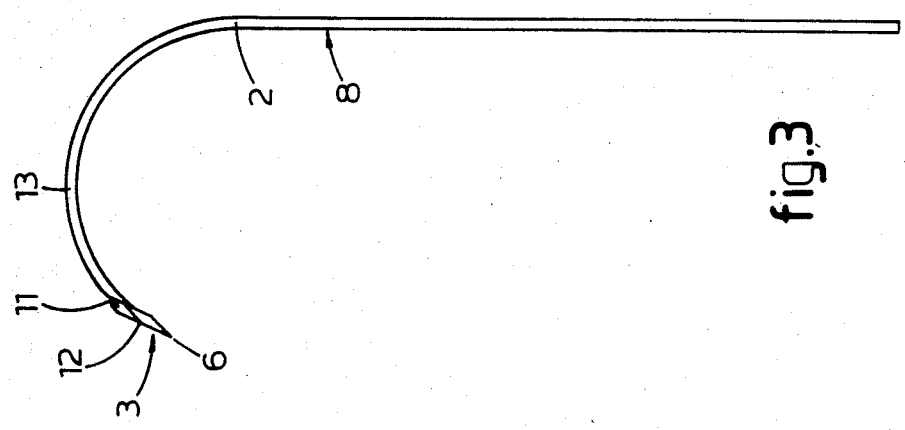
FIG. 3 is a side view of the suture needle according to FIG. 2.

FIGS. 2 and 3 show a suture needle 8 which is especially suited for use more than once. The suture needle 8 like the suture needle 1 comprises a metal shank 2 and a diamond plate 3 attached to one end thereof. This diamond plate 3 in this case is provided with a recess 9 in which a suture thread 10 can be received. Thereby the suture thread 10 can be drawn through the tissue together with the suture needle 8 in order to close a wound. The suture needle 8 can be held constantly in the pair of tweezers without the necessity of releasing and regrasping the suture needle several times during making the suture.

The suture needles 1 and 8 described are made as follows. From a diamond plate obtained in a usual manner little square logs are made with a cross-section of 0.2×0.2 mm, for example. From such logs the diamond plates 3 are cut with main surfaces extending obliquely with respect to the longitudinal axis of the log at an angle of 60°. The thickness of the diamond plates 3 amounts for example upto about 0.22 mm. In order to form the recess 9 a little section of for example 50×50μ is cut out parallel to a main surface. This main surface of the diamond plate 3 is metalized with a titanium-copper-silver or gold-tantalum alloy in a manner known per se.

Thereafter a metal shank with a diameter of 0.2 mm, for example, and with the desired length is cut from a wire. At one end of the metal shank 2 so obtained an end face 11 is ground which also extends obliquely with respect to the longitudinal axis of the shank at an angle of 60°. This oblique end face 11 is also metalized with a titanium-copper-silver or a gold-tantalum alloy.

Thereafter, both metalized faces of the shank 2 and the diamond plate 3 are attached to each other by placing said metalized faces against each other at elevated temperature, whereby the metalized layers diffuse into each other and a strong connection is formed. The superfluous material of the titanium-copper-silver or gold-tantalum alloy is removed. Subsequently the suture needle 1 or 8, respectively is clamped in a grinding holder so that the free main surface 12 can be ground in order to provide the diamond plate with a sharp tip and cutting edges. Finally, the metal shank 2 is provided with the desired bend 13.

Of course the strength of the connection obtained can be controlled.

Figure 4:
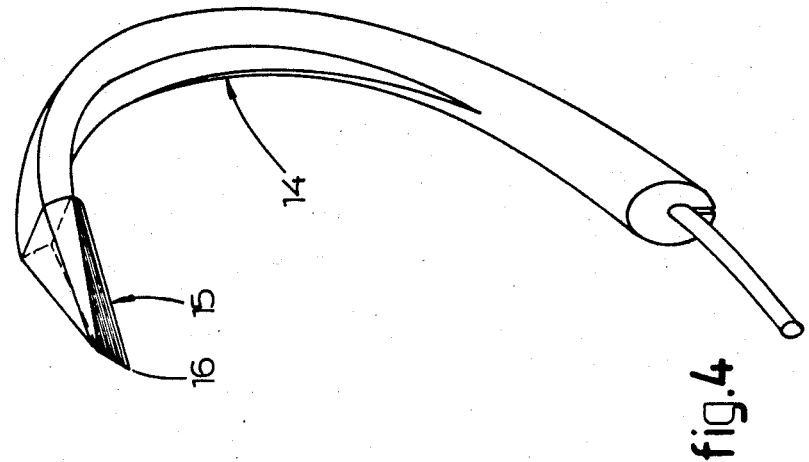
FIG. 4 is a perspective view of a third embodiment of the suture needle according to the invention also connected with a suture thread.

FIG. 4 shows a suture needle 14 mainly corresponding with the suture needle 1 shown in FIG. 1. The manufacturing of the suture needle 14 mainly takes place in the above-described manner, wherein however a usual suture needle without diamond plate forms the starting point.

The suture needle 14 is provided with a triangular diamond plate 15 obtained by cutting through a diamond plate 3 made in the described manner along the short diagonal parallel to the longitudinal axis. In the suture needle 14 shown one of the main surfaces of the triangular diamond plate 15 is bevelled but this is not necessary. The tip 16 of the diamond plate 15 can be reground by making a small facet on the tip.

By means of the described method microsurgical suture needles are obtained with very sharp tips and cutting edges whereby the penetration capacity of the suture needle in tissue is very good. The pressure which has to be exerted on the needle during suturing a wound in order to penetrate the tissue is thus low, so that uncontrolled movements are obviated. The suture needles described here are especially suited for eye surgery, wherein during suturing an eye wound the edges will deform less and the chance of losing eye fluid is significantly decreased. Moreover the described suture needles produce smaller wounds so that the recovery is favourably affected and the deformation of the eyeball will be less.

The described suture needles are suited for repeated use and can be reground, if required.

It is noted that said oblique faces of the diamond and the shank may also extend obliquely at a different angle than 60°.

Although in the above embodiments diamond plates are used it is also possible to use different types of precious stone such as ruby. However, diamond is to be preferred.

The invention is not restricted to the above-described embodiments which can be varied in a number of ways within the scope of the invention.

We claim:

1. Micorsurgical suture needle comprising a precious stone plate formed with main surfaces extending obliquely with respect to the longitudinal axis, an end face extending correspondingly obliquely with respect to the longitudinal axis being ground at one end of a metal shank, on which the precious stone plate is attached with one main surface on the oblique end face of the metal shank, wherein the other main surface of the precious stone plate is ground and provided with a sharp tip and cutting edges.

2. Microsurgical suture needle according to claim 1, wherein a recess is provided in the precious stone plate at the side of the metal shank.

3. Microsurgical suture needle according to claim 1, wherein the precious stone plate consists of diamond.

* * * * *